United States Patent [19]

Baldwin et al.

[11] Patent Number: 4,588,824

[45] Date of Patent: May 13, 1986

[54] PREPARATION OF EPIHALOHYDRIN ENANTIOMERS

[75] Inventors: John J. Baldwin, Gwynedd Valley; David E. McClure, Lansdale, both of Pa.

[73] Assignee: Merck & Co., Inc., Rahway, N.J.

[21] Appl. No.: 505,041

[22] Filed: Jun. 16, 1983

Related U.S. Application Data

[60] Division of Ser. No. 369,724, Apr. 19, 1982, Pat. No. 4,408,063, which is a continuation-in-part of Ser. No. 176,236, Aug. 8, 1980, abandoned, which is a continuation of Ser. No. 940,681, Sep. 8, 1978, abandoned, which is a continuation-in-part of Ser. No. 919,590, Jun. 27, 1978, abandoned.

[51] Int. Cl.[4] .......................................... C07D 317/00
[52] U.S. Cl. ................................................ 549/453
[58] Field of Search .................................... 549/453

[56] References Cited

U.S. PATENT DOCUMENTS 4,360,694  11/1982  Kinnunen et al. ................. 549/454

OTHER PUBLICATIONS

Pfeiffer et al, J. Org. Chem. 35, (1970), p. 221.

*Primary Examiner*—Ethel G. Love
*Attorney, Agent, or Firm*—Alice O. Robertson; Salvatore C. Mitri; Michael C. Sudol, Jr.

[57] ABSTRACT

Processes for preparing (S) or (R) epihalohydrin and an (S) substituted glycerol intermediate are disclosed.

4 Claims, No Drawings

PREPARATION OF EPIHALOHYDRIN ENANTIOMERS

CROSS REFERENCE TO RELATED APPLICATIONS

This application is a division of Ser. No. 369,724, filed Apr. 19, 1982, now U.S. Pat. No. 4,408,063, which in turn is a continuation-in-part of Ser. No. 176,236, filed Aug. 8, 1980, now abandoned, which in turn is a continuation of Ser. No. 940,681, filed Sept. 8, 1978, now abandoned, which in turn is a continuation-in-part of Ser. No. 919,590, filed June 27, 1978, now abandoned.

BACKGROUND OF THE INVENTION

The present invention is concerned with processes for preparing epihalohydrin enantiomers and intermediates.

Epibromohydrin enantiomers have been prepared by a resolution process—and an epichlorohydrin enantiomer has been prepared from 1-bromo-3-chlorpropan-2-ol enantiomer derived from the epibromohydrin [Chemische Berichte 48, 1862-184, (1915)].

An improved method for preparing the epihalohydrin enantiomers from sulfonyloxyhaloalcohol has been discovered—and an improved process for preparing an intermediate useful in the synthesis has also been discovered.

SUMMARY OF THE INVENTION

Process for (a) preparing (S) or (R) epihalohydrin from an (S) or (R) sulfonyloxyhaloalcohol and (b) preparing (S) glycerol-1,2-acetonide from isopropylidine-D-mannitol.

DESCRIPTION OF THE PREFERRED EMBODIMENTS

An embodiment of the present invention is a process for preparing an enantiomer of epihalohydrin which comprises treating an enantiomer of an alcohol having the formula $$Z-SO_2-O-CH_2-\underset{\underset{\displaystyle}{|}}{\overset{\overset{\displaystyle OH}{|}}{CH}}-CH_2-X \qquad (I)$$

wherein Z is phenyl, monosubstituted phenyl, $CF_3$ or $C_1-C_6$ alkyl and X is Cl or Br with an alkali metal glycolate and recovering said epihalohydrin by distillation.

The reaction is illustrated by the following equation:

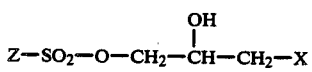

(S) or (R)—FORMULA I $\xrightarrow{\text{GLYCOLATE}}$ (I$^1$)

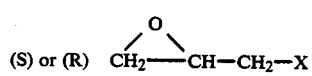

(S) or (R) $CH_2\overset{\displaystyle O}{\overbrace{\phantom{XXX}}}CH-CH_2-X$

The product is recovered in good yield by direct vacuum distillation at room temperature from the reaction mixture.

Z may be phenyl, monosubstituted phenyl or $C_1-C_6$ alkyl. The monosubstituted phenyl group is exemplified by $C_1-C_3$-alkylphenyl e.g., p-propylphenyl, o-methylphenyl, and m-ethylphenyl, p-$NO_2$-phenyl, p-$OCH_3$-phenyl, 2-chlorophenyl and the like. The $C_1-C_6$ alkyl group includes $CH_3$, $C(CH_3)_3$, isopropyl, n-hexyl and the like. The p-methylphenyl and $CH_3$ groups are preferred.

The alkali metal glycolate includes K or Na ethylene glycolate, with Na ethylene glycolate being preferred.

When a more conventional low boiling solvent/strong base, e.g., methanol/$NaOCH_3$ is used in place of the glycolate in reaction (I$^1$), the product yield obtained on direct vacuum distillation at room temperature is low.

Another embodiment of the present invention is a process for preparing (S)-glycerol-1,2-acetonide of the formula

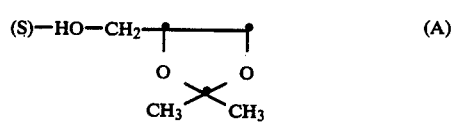

which comprises (a) treating 1,2:5,6-di-O-isopropylidine-D-mannitol having the formula

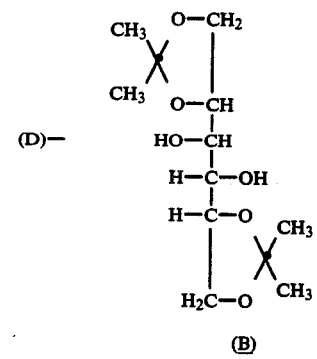

with lead tetraacetate in a suitable solvent and (b) reducing the reaction product from (a) with alkali metal borohydride and (c) treating the reaction mixture from (b) with an ammonium halide.

Suitable solvents include aprotic compounds such as tetrahydrofuran (THF), ethylacetate, dimethylformamide (DMF) and the like. THF and ethylacetate are preferred solvents.

Ammonium halides include $NH_4Br$ and $NH_4Cl$. $NH_4Cl$ is preferred.

The reaction of (B) with $Pb(OAc)_4$ in step (a) may be carried out at any convenient temperature. Temperature below about 10° C. are preferred. The preferred molar nature of lead tetraacetate to (B) is about 1:1.

The reduction of the step (b) is also carried out at a convenient temperature. Preferred temperatures are below about 10° C. The $NaBH_4$ reducing agent is generally added to the reaction mixture in solution e.g., in aqueous NaOH. The amount of $NaBH_4$ may be varied. It is preferred that about 2 moles of $NaBH_4$ per mole of (B) reactant be used.

The reaction of step (b) is allowed to proceed for a period sufficient for the reaction to be complete, e.g., for about 30 minutes at about 0° C. and for about 90 minutes at room temperature. At the appropriate time, $NH_4Cl$ is added to solution until the pH reaches about 8. After the reaction solvent is removed under reduced pressure, the product (A) is recovered using conventional procedures.

When sodium periodate [Synthesis 423 (1977); Biochemistry 3, 976 (1964)] is used in place of Pb(OAc)₄ the product obtained is generally racemic.

When H₂/Raney nickel [J. Biol. Hem. 128, 463 (1939)] is used in place of the NaBH₄, yields obtained are variable depending on the quality of the Raney nickel.

The formula (A) glycerol is especially useful as an intermediate in the preparation of (S) and (R) epihalohydrins. The following flow sheet illustrates this utility:

and 6 has been carried out with racemic reactants [Bull. Chem. Soc. Japan 39, 413 (1966)].

The preparation illustrated by the flow sheet shows that either the (S) or (R) enantiomer of an epihalohydrin, especially epichlorohydrin, can be prepared directly from a common starting material [compound (A) or product (B)] without requiring costly and inefficient resolution procedures. This constitutes another aspect of the present invention.

Epihalohydrins have wide utility in organic synthesis. The enantiomers of epihalohydrin may be especially

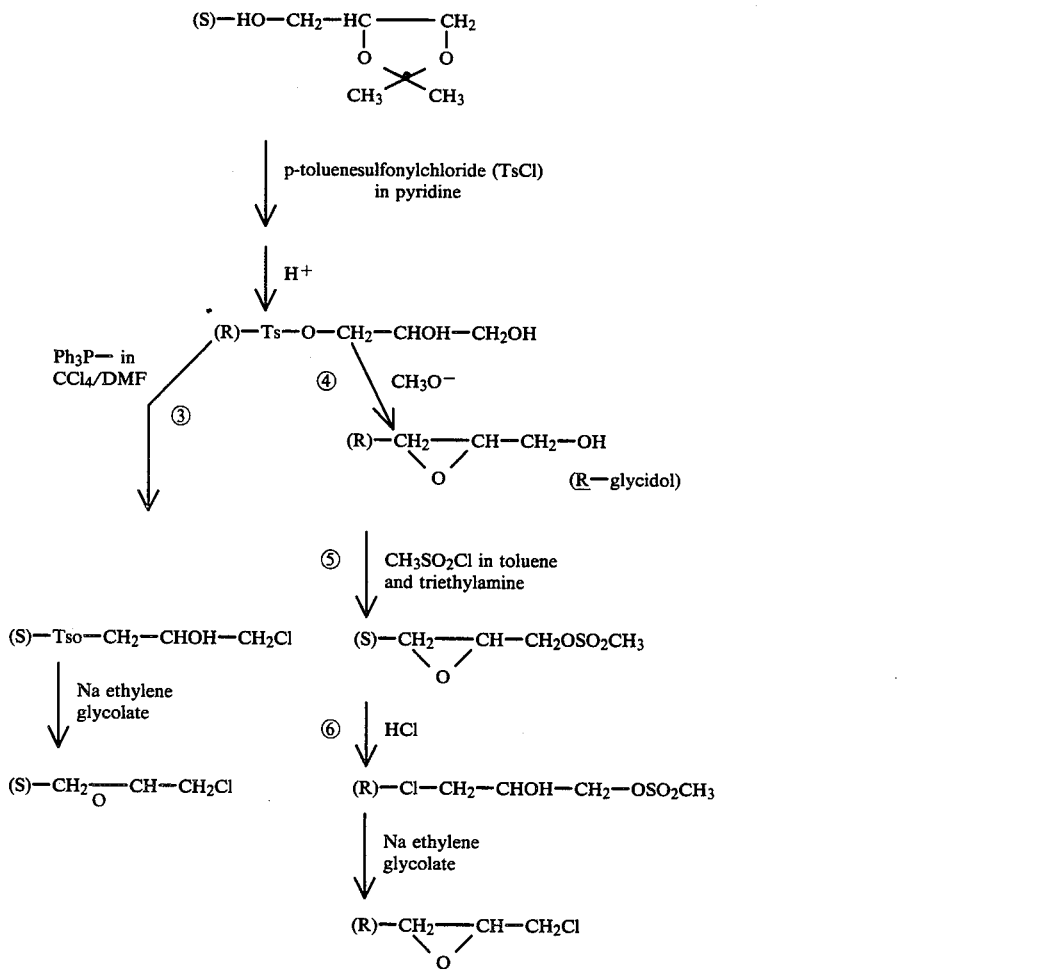

Reactions related to 1 and 2 are disclosed in J.A.C.S. 64, 1291 (1942). Reaction 3 is related to that described in Tetrahedron Letters, 4361 (1969). Reaction sequence 5 useful to prepare intermediates which in turn can be used to prepare specific isomers which have pharmaceutical utility. One such preparation is illustrated by the following reaction equations:

REACTION SEQUENCE A

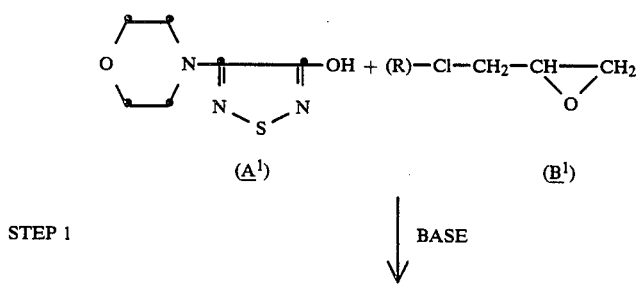

STEP 1      BASE

REACTION SEQUENCE A

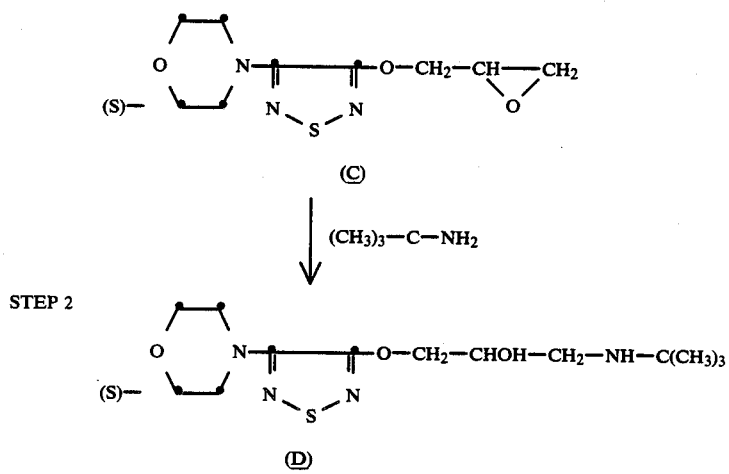

STEP 2

The product (D) is a commercial β-adrenergic blocking agent.

Other preparations utilizing the Step 1, sequence A type reaction are illustrated by the following reaction equation:

REACTION B

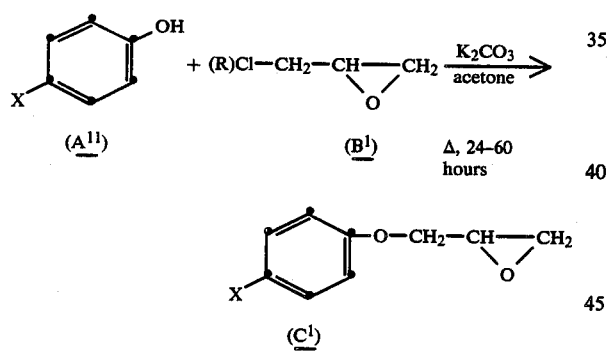

X in this equation is H, CHO, CN or OCH$_3$.

Where a stronger base, such as NaH in DMF, is used in the above reactions, the intermediate (C or C$^1$) is obtained as a mixture of (S) and (R) isomer.

Another aspect of the present invention relates to the novel sulfonyl intermediates of the type obtained in Step (5) in the above flow sheet. These compounds are represented by the formula

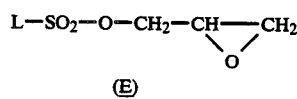

where L may be an alkyl group such as CH$_3$, C$_4$H$_9$, CF$_3$— and the like, or a phenyl group such as phenyl, p-chlorophenyl, p-tolyl, p-nitrophenyl and the like.

The formula (E) compounds are useful as intermediates in reactions related to Reactions A and B as illustrated by the following equation:

REACTION C aryl-OH + L—SO$_2$O—CH$_2$—CH———CH$_2$
  (F)                                    O
                                       (E)

↓ base aryl-O—CH$_2$—CH———CH$_2$
                         O
(G)

aryl includes groups such as phenyl,

where X is a substituent such as chloro, CHO, CN, C$_1$-C$_4$alkoxy and the like; pyridyl, cyanopyridyl 4-morpholino-1,2,5-thiadiazolyl and the like.

When an enantiomer i.e., (R) or (S) isomer, of the (E) compound is used in the reaction, the type of base and the L group have an effect on the isomer configuration of the final product. Illustrating this effect are the following two equations:

REACTION D

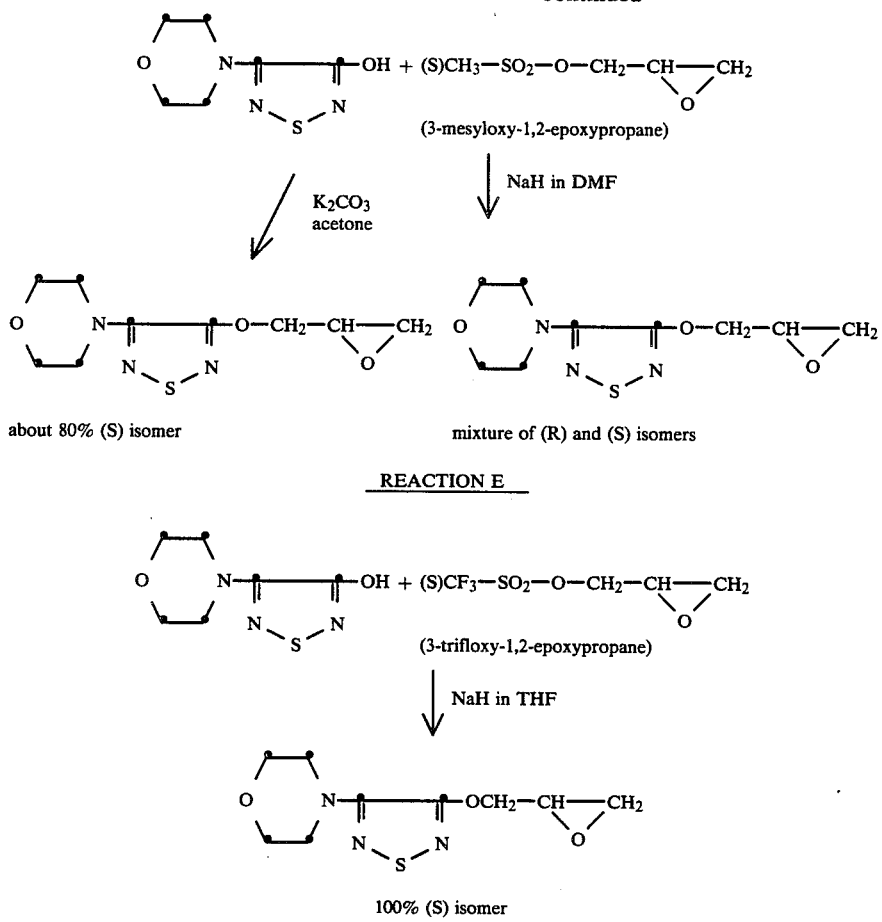

REACTION E

Thus, where L is CF₃ and a strong base is used, the (S) isomer of the formula (E) compounds yields the (S) isomer of the formula (G) compound. Therefore, by utilizing an enantiomer of 3-trifloxy-1,2-epoxypropane and a suitable base in the (C) reaction the isomeric configuration of the trifloxy enantiomer is maintained in the product. If an enantiomer of mesyloxy mesyloxyepoxypropane is used, a mixture of enantiomers is obtained.

The following example describes the preparation of (S)-3-trifloxy-1,2-epoxypropane. All temperatures are in °C.

EXAMPLE A

To pyridine (10.3 g, 0.13 m) in CH₂Cl₂ (300 ml) cooled to −23° in a dry ice/CCl₄ bath was added trifluoromethanesulfonic anhydride (36.7 g, 0.13 m) in CH₂Cl₂ (100 ml) dropwise over ½ hour. While still cooling this mixture at −23°, (R)-glycidol (8.6 g, 0.116 m) in CH₂Cl₂ (100 ml) was added dropwise over ½ hour. After stirring for 5 minutes with cooling and 15 minutes without, an equal volume of hexane was added and the solids were filtered. Concentration of the solution at 30°/25 torr. left a residue which was distilled to give (S)-3-trifloxy-1,2-epoxypropane (40%); bp 35°–39°/0.2 mm; $[\alpha]_D^{24} = 14.7°$ (c=3.90, CHCl₃); 1H NMR (CDCl₃) 4.8 (1H, d of d, J=11, J=3), 4.4 (1H, d of d, J=11, J=3), 3.3 (1H, m), 2.9 (1H, t, J=4.5), 2.7 (1H, J=4.5, J=2).

The following examples illustrate the processes of the present invention. All temperatures are in °C.

EXAMPLE 1

(S)-Glycerol-1,2-acetonide

To an ice-cooled solution of 1,2:5,6-di-O-isopropylidine-D-mannitol (80.0 g, 0.3 ml) in THF (400 m) was added portionwise with stirring dry Pb(OAc)₄ (134 g, 0.3 m), while maintaining the temperature below 10° C. The solution was stirred for 30 minutes with ice cooling and an additional 30 minutes without. After filtering through Super-Cel and cooling in an ice bath, a solution of NaBH₄ (22.9 g, 0.62 m) in 4% aqueous NaOH (400 ml) was added dropwise with vigorous stirring while maintaining the temperature below 10° C. After stirring in an ice bath for 30 minutes and at room temperature for 90 minutes, solid ammonium chloride was added to the solution until it buffered at about pH 8. The THF was removed under reduced pressure, and the resulting aqueous solution was saturated with NaCl. After extracting into ethyl acetate, the organic layer was washed with 5% aqueous NaOH saturated with NaCl, dried (Na₂SO₄), and concentrated. Distillation afforded pure (S)-glycerol-1,2-acetonide (58.4 g, 73%); bp 80°–90° C./20 mm; ¹H NMR (CDCl₃) 1.45 (6H, s), 3.5–4.5 (6H, m); $[\alpha]_D^{25} = 11.3°$ (c=5.174, CH₃OH).

EXAMPLE 2

(a) (R)-3-Tosyloxy-1,2-propanediol

To an ice-cooled solution of (S)-glycerol-1,2-acetonide (72.0 g, 0.55 m) in pyridine (300 ml) was added portionwise with stirring p-toluenesulfonyl chloride (104.0 g, 0.55 m). After standing in a refrigerator for 16 hours, the reaction mixture was diluted with ether (300 ml), washed with 1N HCl until the aqueous wash was acidic, and then washed with saturated aqueous NaHCO$_3$. The ether layer was dried (Na$_2$SO$_4$) and concentrated to give (R)-3-tosyloxypropanediol acetonide (141.0 g, 91%), which was used without further purification.

The acetonide from above in acetone (100 ml) and 1N HCl (300 ml) was heated on a steam bath for 30 minutes. The resulting solution was concentrated to dryness, and the residue was dissolved in CH$_2$Cl$_2$. After drying (Na$_2$SO$_4$) and concentration, the resulting oil solidified upon standing. Residual solvents were removed at 25° C. and 0.5 mm over 18 hours to give (R)-3-tosyloxy-1,2-propanediol, (121.0 g, 100%); mp 54°–59° C. (lit=61°–63° C.); $^1$H NMR (CDCl$_3$) 2.4 (3H, s), 3.3–4.3 (7H, m), 7.35 and 7.8 (4H, 2d, J=8).

(b) (R)-Glycidol

To an ice-cooled solution of (R)-31-tosyloxy-1,2-propanediol (120.5 g, 0.49 m) in methanol (200 ml) and ether (100 ml) was added sodium pellets (10.7 g, 0.45 m) in three portions over approximately 1 hour. Stirring was continued with ice cooling for 1 hour. The reaction mixture was concentrated at 30° C., and the residue was taken up in ether. After filtration, the solvent was removed at 30°C./25 mm, and the residue was treated with chloroform and reconcentrated to remove the last traces of methanol. An additional chloroform treatment as above gave (R)-glycidol (33.5 g, 93%), which was used without purification in subsequent steps.

(c) (S)-3-Mesyloxy-1,2-epoxypropane

To an ice-cooled solution of (R)-glycidol (5.0 g, 0.068 m) and triethylamine (8.1 g, 0.080 m) in toluene (100 ml) was added, over 15 minutes, methanesulfonyl chloride (8.0 g, 0.070 ml) in toluene (25 ml). Stirring was continued with cooling for 1 hour. The solution was filtered and concentrated to give an 80–85% yield of the crude (S)-3-mesyloxy-1,2-epoxypropane; this material could be used without further purification. Distillation gave 7 (61%); bp 92°–95° C./0.1 mm; $[\alpha]_D^{22}$=23.7° (c=5.16, CH$_3$OH); $^1$H NMR (CDCl$_3$) 4.5 (1H, d of d, J=12, J=3), 4.1 (1H, d of d, J=12, J=6), 3.3 (1H, m), 3.1 (3H, s), 2.8 (2H, m).

(d) (R)-Epichlorohydrin

Concentrated HCl (20 ml) was added to (S)-3-mesyloxy-1,2-epoxypropane (5.0 g, 0.033 m) over 15–20 minutes. After stirring for an additional 30 minutes, the water was removed through the addition and subsequent evaporation of ethanol. Finally, residual ethanol was removed at room temperature and 0.1 mm to give (R)-3-mesyloxy-2-hydroxy-1-chloropropane, (5.4 g, 85%); $^1$H NMR (CDCl$_3$) 4.35 (2H, d), 4.1 (1H, m), 3.65 (2H, d), 3.1 (3H, s), 2.9 (1H, broad s); $[\alpha]_D^{22}$=7.1° (c=5.78, CH$_3$OH).

To (R)-3-mesyloxy-2-hydroxy-1-chloropropane (5.4 g, 0.029 m) in dry ethylene glycol (20 ml) was added a solution of sodium ethylene glycolate [from sodium pellets (0.8 g, 0.034 ml)] in dry ethylene glycol (20 ml). After stirring for 15 minutes, (R)-epichlorohydrin (2.2 g, 86%) was distilled from the reaction mixture at room temperature and 0.2 mm and trapped in dry ice/acetone; $^1$H NMR (CDCl$_3$) & 3.6 (2H, d), 3.2 (1H, m), 2.8 (2H, m); $[\alpha]_D^{22}$=33.0° (c=4.22, CH$_3$OH).

A small sample was further purified by preparative GC on an HP 5710 A instrument using a 6' 5% OV-17 column with an oven temperature of 60° C. to give (R)-epichlorohydrin; $[\alpha]_D^{23}$=34.3° (c=1.50, CH$_3$OH).

EXAMPLE 3

(S)-Epichlorohydrin

To triphenylphosphine (13.2 g, 0.05 m) in CCl$_4$ (20 ml) and DMF (50 ml), (R)-3-tosyloxy-1,2-propanediol (12.3 g, 0.05 m) in DMF (50 ml) was added all at once. After the addition was complete, the temperature increased to 50° C. over 15 minutes. The mixture was then allowed to stir for 3 hours. The residual solvents were removed (50° C., 2 mm) and the residue was taken up in H$_2$O, dried (Na$_2$SO$_4$), and concentrated. Residual solvents were removed at 25° C. and 0.2 mm over 18 hours.

To this residue, composed of triphenylphosphine oxide and (S)-3-tosyloxy-2-hydroxy-1-chloropropane, in dry ethylene glycol (50 ml) was added a solution of sodium ethylene glycolate [from sodium pellets (1.25 g, 0.054 m)] in dry ethylene glycol (50 ml). After stirring for 15 minutes, (S)-epichlorohydrin was distilled from the reaction mixture at room temperature and 0.2 mm and trapped in dry ice/acetone. The $^1$H NMR indicated that traces of CH$_2$Cl$_2$ and H$_2$O were present; $[\alpha]_D^{20}$=28.1° (c=2.47, CH$_3$OH).

A small sample was purified by preparative GC to yield pure (S)-epichlorohydrin $[\alpha]_D^{23}$=33.0° (c=2.47, CH$_3$OH).

Analogous epibromohydrins are obtained when the corresponding bromo reactants replace the chloro reactants in Examples 2 and 3.

The following examples illustrate low yields obtained when low boiling solvent/strong base systems are used instead of the glycolate system of the present invention, e.g., Example 2(d) or Example 3. All temperatures are in °C.

EXAMPLE 4

Epichlorohydrin

Concentrated HCl (20 ml) was added to 3-mesyloxy-1,2-epoxypropane (5.0 g, 0.033 m) over 15–20 minutes. After stirring for an additional 30 minutes, the water was removed through the addition and subsequent evaporation of ethanol. Finally, residual ethanol was removed at room temperature and 0.1 mm to give 3-mesyloxy-2-hydroxy-1-chloropropane (5.4 g, 85%).

To 0.95 g (0.005 m) of this crude mesylate was added NaH (0.25 g, 50% oil dispersion, 0.005 m). After stirring for 30 minutes, the mixture was filtered and the solvent was removed on a rotary evaporator at 30°/25 mm to give epichlorohydrin (0.20 g, 43%). The proton NMR of this compound indicated the presence of some (~10%) of the corresponding 3-mesyloxy-1,2-epoxypropane.

Several other reactions of the Example 4 type were run in order to probe the effectiveness of various base/solvent combinations. Although the use of NaH/CH$_3$OD for an NMR study indicated essentially quantitative production of epichlorohydrin, none of the other base/solvent combinations (see table below) gave better yields than the 43% in Example 4.

TABLE

| Base/Solvent | Crude Yield of Epichlorohydrin |
| --- | --- |
| NaH/ether | 20% |
| NaH/THF | none |
| NaH/CH$_2$Cl$_2$ | 40% |
| n-BuLi/ether-hexane | 30% |
| aqueous NaOH/H$_2$O—ether | none |

EXAMPLE 5

(R)-Epichlorohydrin

Concentrated HCl (75 ml) was added to (S)-3-mesyloxy-1,2-epoxypropane (6.8 g, 0.045 m). After stirring for 30 minutes, the water was removed through the addition and subsequent evaporation of ethanol. Finally, the residual ethanol was removed at room temperature and 0.1 mm to give (R)-3-mesyloxy-2-hydroxy-1-chloropropane (7.8 g, 92%). This material was dissolved in ether (50 ml) and methanol (10 ml) in an ice bath and sodium (0.94 g, 0.041 m) was added. After stirring for one hour, the mixture was filtered and concentrated at 30°/25 mm. Added acetone, filtered and reconcentrated at 30°/25 mm. Attempted distillation of the residue led to total decomposition; none of the desired (R)-epichlorohydrin was obtained.

Claims to the invention follow.

What is claimed is:

1. A process for preparing (S)-glycerol-1,2-acetonide which comprises:
   (a) treating 1,2:5,6-di-O-isopropylidine-D-mannitol with lead tetraacetate in an aprotic solvent,
   (b) reducing the reaction product from (a) with an alkali metal borohydride and
   (c) treating the reaction mixture containing the reduced product with an ammonium halide to obtain said (S)-glycerol derivative.

2. The process of claim 1 wherein said solvent is tetrahydrofuran.

3. The process of claim 2 wherein said ammonium halide is NH$_4$Cl.

4. The process of claim 3 wherein sufficient halide is added to lower the solution pH to about 8.

* * * * *